(12) United States Patent
Ranganathan et al.

(10) Patent No.: US 10,226,185 B2
(45) Date of Patent: Mar. 12, 2019

(54) TUBE AND SENSOR GUIDE WIRE COMPRISING TUBE

(71) Applicant: ST. JUDE MEDICAL COORDINATION CENTER BVBA, Zaventem (BE)

(72) Inventors: Sathees Ranganathan, Sundbyberg (SE); Anna Norlin-Weissenrieder, Lindingö (SE); Rolf Hill, Järfälla (SE); Erik Hansson, Uppsala (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 0 days.

(21) Appl. No.: 13/804,342

(22) Filed: Mar. 14, 2013

(65) Prior Publication Data

US 2013/0296718 A1    Nov. 7, 2013

Related U.S. Application Data

(60) Provisional application No. 61/642,101, filed on May 3, 2012.

(51) Int. Cl.
*A61B 5/00* (2006.01)
*A61M 25/00* (2006.01)
(Continued)

(52) U.S. Cl.
CPC .............. *A61B 5/02* (2013.01); *A61B 5/0215* (2013.01); *A61B 5/6851* (2013.01);
(Continued)

(58) Field of Classification Search
CPC .......... A61M 25/0051; A61M 25/0054; A61M 25/0013; A61M 25/0138; A61M 25/0029;
(Continued)

(56) References Cited

U.S. PATENT DOCUMENTS 3,521,620 A    7/1970   Cook
4,456,013 A    6/1984   De Rossi et al.
(Continued)

FOREIGN PATENT DOCUMENTS

DE    24 20 610 A1    10/1975
EP    0 387 453 A1    9/1990
(Continued)

OTHER PUBLICATIONS

International Preliminary Report on Patentability, PCT/IB2013/000903, dated Nov. 13, 2014, 11 pages.
(Continued)

*Primary Examiner* — Rene Towa
*Assistant Examiner* — H. Q. Nguyen
(74) *Attorney, Agent, or Firm* — Foley & Lardner LLP

(57) ABSTRACT

A tube for an intravascular medical device has a longitudinal extension along a longitudinal axis. The tube comprises a tube wall having a specified thickness and a plurality of through-going slots, wherein each slot has an essentially elongated shape along a main extension extending along the circumference of the tube. At least two slots are provided in a plane perpendicular to the longitudinal axis such that the main extension of the at least two slots are in the perpendicular plane. The lengths of the slots in the same perpendicular plane P are essentially the same, and the lengths L of the slots in different planes vary along the longitudinal extension of the tube according to a predefined pattern. A sensor guide wire for an intravascular measurement of at least one variable in a living body may comprise such a tube.

9 Claims, 11 Drawing Sheets

(51) Int. Cl.
*A61B 5/02* (2006.01)
*A61B 5/0215* (2006.01)
*A61M 25/09* (2006.01)

(52) U.S. Cl.
CPC ........ *A61M 25/0051* (2013.01); *A61M 25/09* (2013.01); *A61M 25/09033* (2013.01); *A61M 2025/0002* (2013.01); *A61M 2025/09133* (2013.01); *A61M 2025/09175* (2013.01)

(58) Field of Classification Search
CPC ........... A61M 2025/0002; A61M 2025/09175; A61M 2025/09133; A61M 25/09; A61B 5/0215; A61B 5/6851
See application file for complete search history.

(56) References Cited

U.S. PATENT DOCUMENTS

| | | | |
|---|---|---|---|
| 4,712,566 A | 12/1987 | Hok | |
| 4,941,473 A | 7/1990 | Tenerz et al. | |
| 5,018,529 A | 5/1991 | Tenerz et al. | |
| 5,085,223 A | 2/1992 | Lars et al. | |
| 5,125,058 A | 6/1992 | Tenerz et al. | |
| 5,437,288 A * | 8/1995 | Schwartz et al. | 600/585 |
| 5,549,109 A | 8/1996 | Samson et al. | |
| RE35,648 E | 11/1997 | Tenerz et al. | |
| 5,993,378 A | 11/1999 | Lemelson | |
| 6,019,728 A | 2/2000 | Iwata et al. | |
| 6,045,734 A | 4/2000 | Luther et al. | |
| 6,162,182 A | 12/2000 | Cole | |
| 6,167,763 B1 | 1/2001 | Tenerz et al. | |
| 6,248,083 B1 | 6/2001 | Smith et al. | |
| 6,295,990 B1 | 10/2001 | Lewis et al. | |
| 6,491,712 B1 | 12/2002 | O'Connor | |
| 7,011,636 B2 | 3/2006 | Tenerz | |
| 7,222,539 B2 | 5/2007 | Tulkki | |
| RE39,863 E | 10/2007 | Smith | |
| 7,724,148 B2 | 5/2010 | Samuelsson et al. | |
| 8,174,395 B2 | 5/2012 | Samuelsson et al. | |
| 8,461,997 B2 | 6/2013 | Samuelsson et al. | |
| 8,551,022 B2 | 10/2013 | Von Malmborg | |
| 9,144,664 B2 | 9/2015 | Jacobsen et al. | |
| 2002/0013540 A1 | 1/2002 | Jacobsen et al. | |
| 2002/0049392 A1* | 4/2002 | DeMello | 600/585 |
| 2002/0077520 A1 | 6/2002 | Segal et al. | |
| 2002/0173785 A1 | 11/2002 | Spear et al. | |
| 2003/0009208 A1* | 1/2003 | Snyder et al. | 607/116 |
| 2003/0069522 A1* | 4/2003 | Jacobsen | A61M 25/0013 600/585 |
| 2005/0004515 A1 | 1/2005 | Hart et al. | |
| 2005/0043670 A1 | 2/2005 | Rosenberg | |
| 2005/0187487 A1 | 8/2005 | Azizkhan et al. | |
| 2005/0268725 A1 | 12/2005 | Tulkki | |
| 2006/0004346 A1* | 1/2006 | Begg | 604/525 |
| 2006/0211946 A1 | 9/2006 | Mauge et al. | |
| 2007/0088220 A1 | 4/2007 | Stahmann | |
| 2008/0200770 A1* | 8/2008 | Hubinette | 600/300 |
| 2009/0020961 A1 | 1/2009 | Kameyama et al. | |
| 2009/0062602 A1 | 3/2009 | Rosenberg et al. | |
| 2009/0177185 A1 | 7/2009 | Northrop | |
| 2010/0063479 A1 | 3/2010 | Merdan et al. | |
| 2010/0145308 A1 | 6/2010 | Layman et al. | |
| 2010/0152663 A1 | 6/2010 | Darr | |
| 2010/0217304 A1 | 8/2010 | Angel et al. | |
| 2010/0228112 A1 | 9/2010 | Von Malmborg | |
| 2010/0262041 A1 | 10/2010 | Von Malmborg | |
| 2011/0004198 A1 | 1/2011 | Hoch | |
| 2011/0160648 A1 | 6/2011 | Hoey | |
| 2011/0160680 A1* | 6/2011 | Cage et al. | 604/265 |
| 2011/0213220 A1 | 9/2011 | Samuelsson et al. | |
| 2011/0245808 A1 | 10/2011 | Voeller et al. | |
| 2012/0289808 A1 | 11/2012 | Hubinette | |
| 2013/0102927 A1 | 4/2013 | Hilmersson | |
| 2013/0102928 A1 | 4/2013 | Sotos et al. | |
| 2013/0274618 A1 | 10/2013 | Hou et al. | |
| 2013/0296718 A1 | 11/2013 | Ranganathan et al. | |
| 2014/0058338 A1* | 2/2014 | Adams | A61M 25/0021 604/264 |
| 2016/0249821 A1 | 9/2016 | Boye et al. | |
| 2016/0262698 A1 | 9/2016 | Mahlin | |

FOREIGN PATENT DOCUMENTS

| | | |
|---|---|---|
| EP | 0 521 595 B1 | 5/1999 |
| EP | 1 340 516 A1 | 9/2003 |
| EP | 0 877 574 B1 | 10/2003 |
| EP | 1 849 409 A1 | 10/2007 |
| EP | 2 085 108 A2 | 8/2009 |
| EP | 1 545 680 B1 | 9/2010 |
| SE | 441725 B | 11/1985 |
| SE | 453561 B | 2/1988 |
| SE | 454045 B | 3/1988 |
| SE | 460396 B | 10/1989 |
| SE | 469454 B | 7/1993 |
| WO | WO-97/00641 A1 | 1/1997 |
| WO | WO-00/69323 A2 | 11/2000 |
| WO | WO-03/094693 A2 | 11/2003 |
| WO | WO-2004/011076 A2 | 2/2004 |
| WO | WO 2004/011076 A2 | 2/2004 |
| WO | WO-2004/011076 A2 | 5/2004 |
| WO | WO 2007/050718 A1 | 5/2007 |
| WO | WO 2009/020954 A1 | 2/2009 |
| WO | WO 2009/029639 A1 | 3/2009 |
| WO | WO-2009/054803 A1 | 4/2009 |
| WO | WO-2009/112060 A1 | 9/2009 |
| WO | WO-2011/041720 A2 | 4/2011 |
| WO | WO-2012/000798 A1 | 1/2012 |

OTHER PUBLICATIONS

"In", The American Heritage Dictionary of the English Language, Fifth Edition (2014) Houghton Mifflin Harcourt Publishing Company, pp. 1-3, Retrieved from <https://ahdictionary.co/word/search.html?q-IN> on Mar. 25, 2015.
tube.Dictionary.com, Dictionary.com Unabridged, Random House, Inc.,http://dictionary.reference.com/browse/tube> (accessed: Sep. 5, 2014).
USPTO Office Action, U.S. Appl. No. 13/806,380, dated Apr. 1, 2015, 18 pages.
USPTO Office Action, U.S. Appl. No. 13/806,380, dated Sep. 24, 2014, 19 pages.
"-Like". 2011. In the American Heritage Dictionary of the English Language, Boston: Houghton Mifflin. <http://search.credoreference.com/content/entry/hmdictenglang/like/0>.
USPTO Office Action, U.S. Appl. No. 13/806,380, dated Feb. 1, 2016,18 pages.
European Office Action, Application No. 13 723 953.9, Jun. 27, 2017, 6 pages.
USPTO Office Action, U.S. Appl. No. 13/806,380, dated Aug. 4, 2017, 15 pages.
PCT/ISA/206, International Application No. PCT/US2016/019498, 7 pages.
Radi Medical Systems AB, PressureWire Certus, Brochure, 60680 Rev. 03, Apr. 2008.
International Search Report and Written Opinion, PCT/US2016/019498, dated Jul. 4, 2016, 17 pages.
USPTO Office Action, U.S. Appl. No. 13/806,380, dated Jan. 30, 2018, 18 pages.
European Office Action, dated Jul. 20, 2018, 6 pages.
Japanese Office Action and English translation, Application No. 2016-525613, dated Dec. 5, 2017, 6 pages.
Japanese Office Action and English translation, Application No. 2016-525613, dated Mar. 21, 2017, 14 pages.
Machine translation of DE 2420610.
USPTO Office Action, U.S. Appl. No. 13/806,380, dated Oct. 31, 2013, 14 pages.
USPTO Notice of Allowance, U.S. Appl. No. 13/804,342, dated Oct. 18, 2018, 14 pages.
European Extended Search Report, dated Nov. 19, 2018, 6 pages.

(56) References Cited

OTHER PUBLICATIONS

USPTO Office Action, U.S. Appl. No. 13/806,380, dated Oct. 31, 2018, 14 pages.
USPTO Office Action, U.S. Appl. No. 15/030,770, dated Oct. 18, 2018, 14 pages.

* cited by examiner

DETAIL C

SECTION III-III

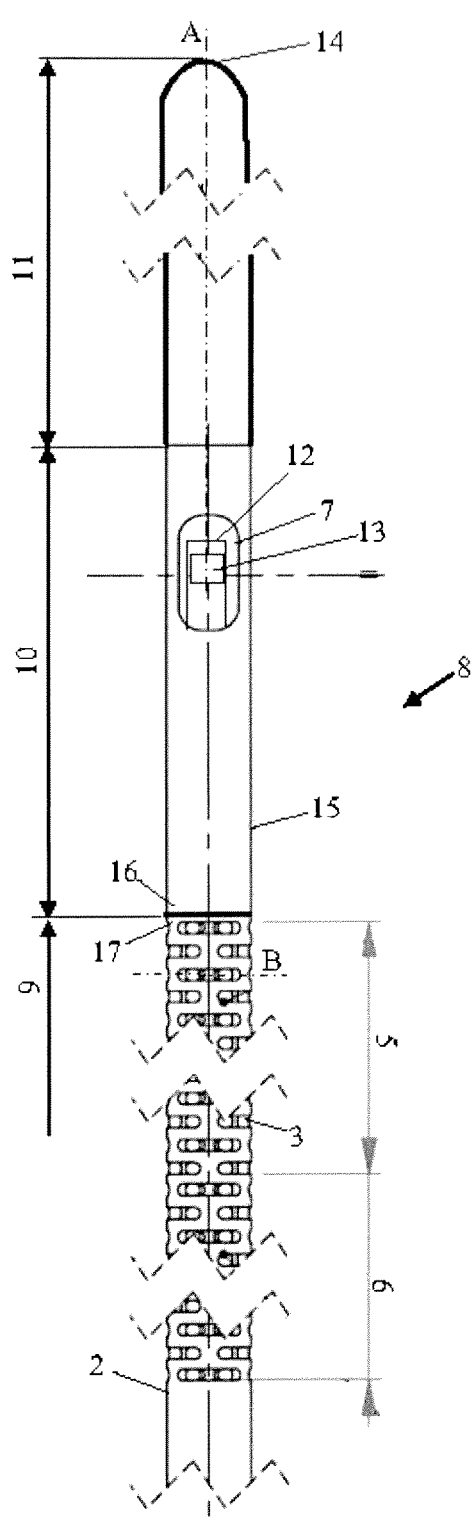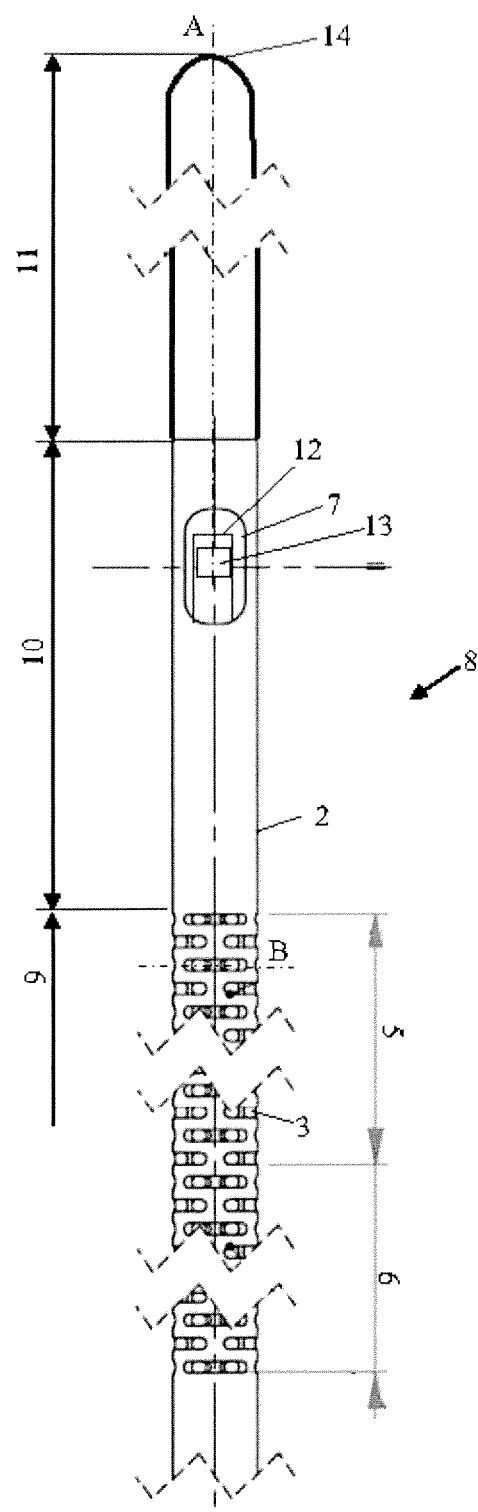
FIG. 6
FIG. 7

Detail E

Detail D

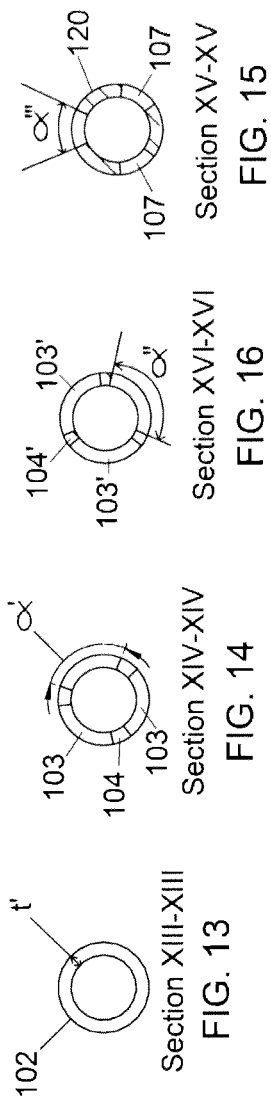

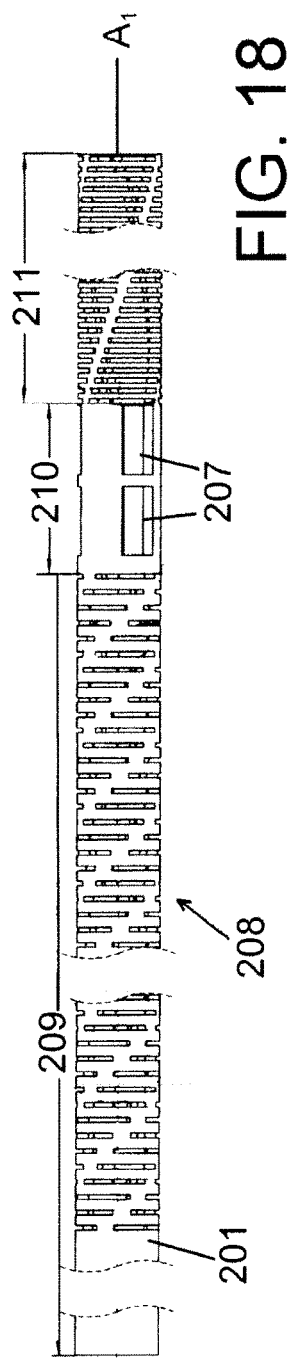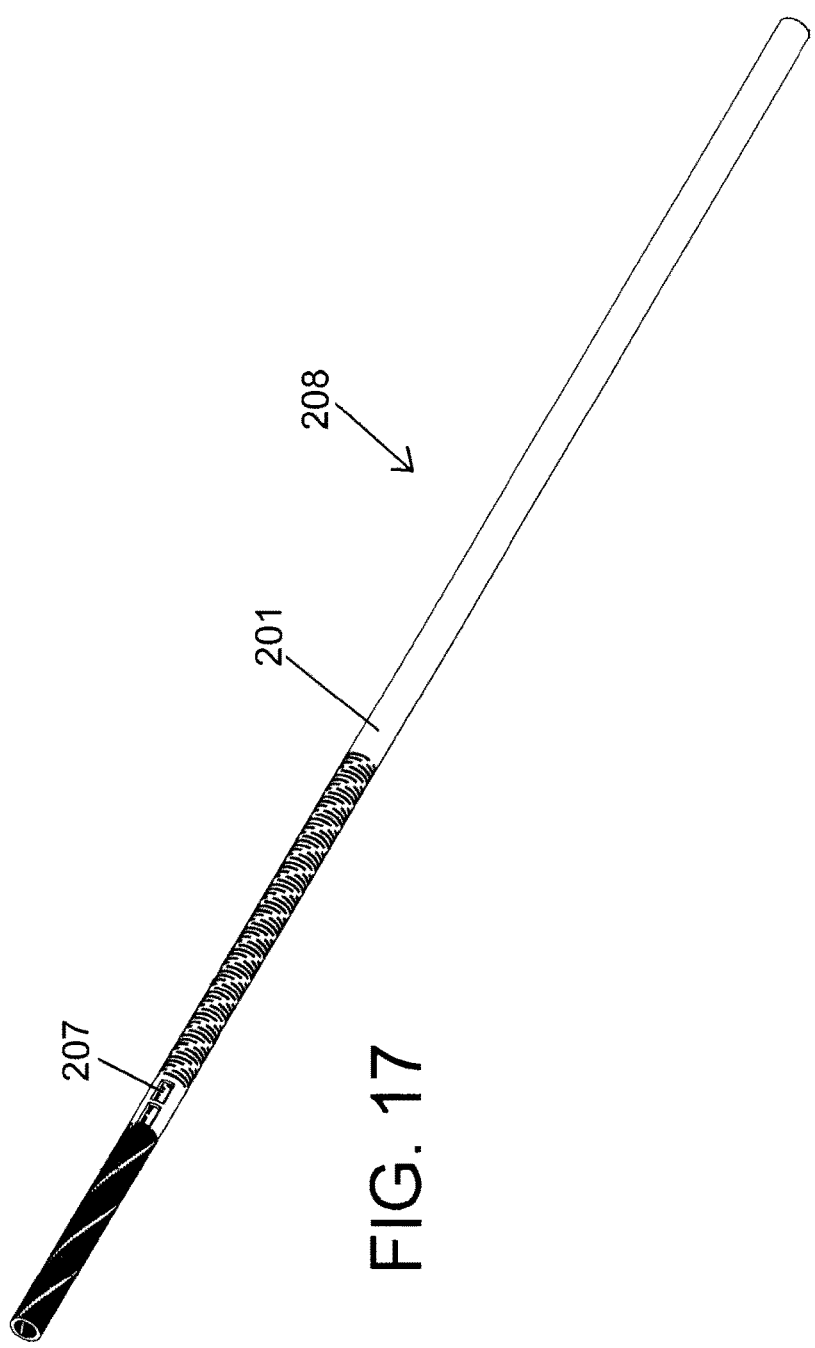

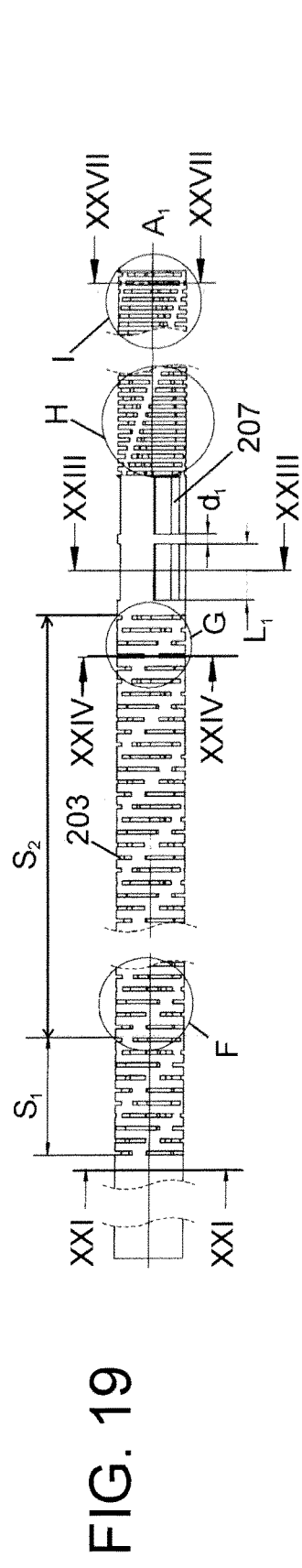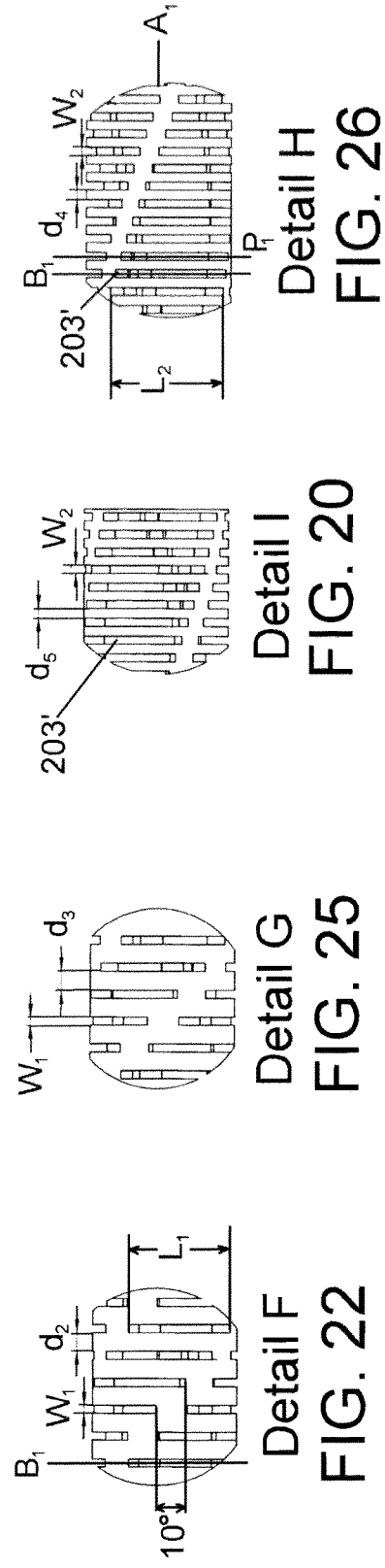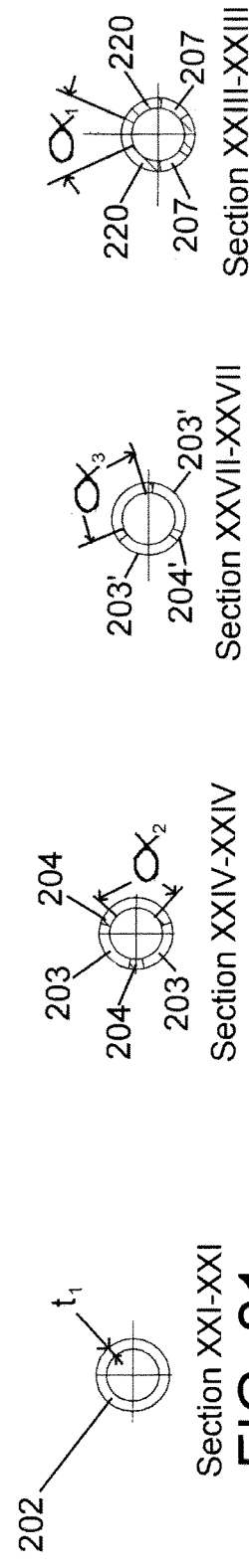

Section XXIX-XXIX

TUBE AND SENSOR GUIDE WIRE COMPRISING TUBE

This application claims priority from U.S. Provisional Application 61/642,101, filed May 3, 2012, incorporated herein by reference in its entirety.

BACKGROUND

The present invention relates to a tube for an intravascular medical device, and in particular to a sensor guide wire comprising such a tube.

Today, there is an increased need for invasive measurements of physiological variables. For example, when investigating cardiovascular diseases, it is strongly desired to obtain local measurements of blood pressure, flow and temperature in order to evaluate the condition of the subject under measurement. Therefore, methods and devices have been developed for disposing a miniature sensor inside the body of an individual at a location where the measurements should be performed, and for communicating with the miniature sensor in order to provide the physician or medical technician with critical information as to the status of a patient's condition. Typically, the miniature sensor is arranged at a distal end of a guide wire, which is generally known in the art, and used for example in connection with the treatment of coronary disease.

The distal end of the guide wire is inserted into the body of a patient, for example into an opening of the femoral artery, and placed at a desired location. Once the guide wire is placed by the physician into the appropriate location, the miniature sensor can measure the blood pressure and/or flow. The measurement of blood pressure is a way to diagnose e.g. the significance of a stenosis. For evident reasons, the dimensions of the sensor and the guide wire are fairly small; the guide wire typically has a diameter of 0.35 mm. The sensor element may, for example, be embodied by an elongated, essentially rectangular chip with a pressure sensitive member in the form of a membrane provided thereon.

In order to power the sensor and to communicate signals representing the measured physiological variable to a control unit acting as an interface device disposed outside the body, one or more microcables for transmitting the signals are connected to the sensor, and are routed along the guide wire to be passed out from the vessel to an external control unit via a connector assembly. Most commonly, extremely thin electrical cables are provided inside the guide wire, which itself is provided in the form of a tube (having an outer diameter of e.g. 0.35 min), oftentimes made of stainless steel. In order to increase the bending strength and maneuverability of the tubular guide wire, a core wire is positioned inside the tube. The mentioned electrical leads are positioned in the space between the inner lumen wall of the tube and the core wire. Furthermore, the sensor chip is often arranged in a short tube, also referred to as a jacket or a sleeve. The jacket is hollow and accommodates, besides the sensor chip, a portion of a core wire and often at least one microcable. A first coil may be attached to the distal end of the jacket, and optionally a second coil may be attached to the proximal end of the jacket. The first and second coils may be attached to the respective end of the jacket, e.g. by gluing, welding or alternatively soldering. One purpose of the first coil is to enable the steering of the sensor guide wire through winding blood vessels. To help the user easily guide the wire through such tortuous vessel systems, the distal coil is often radioopaque, such that it is visible on an angiogram.

A large flexibility of the sensor guide wire can be advantageous in that it allows the sensor guide wire to be introduced into small and tortuous vessels. It should, however, also be recognized that if the core wire is too flexible, it would be difficult to push the sensor guide forward into the vessels, i.e. the sensor guide wire must possess a certain "pushability" and a certain "torquability." Additionally, the sensor guide must be able to withstand the mechanical stress exerted on the core wire especially in sharp vessel bends.

Besides being flexible enough, it can be also important that the sensor guide wire tip responds when steering the sensor guide wire through the tortuous vessels, i.e. the sensor guide wire tip should also have sufficient "steering response." "Steering response" is a measure of the behavior of a sensor guide wire when the sensor guide wire tip is subjected to a non-linear pathway and rotated. The "steering response" of a sensor guide wire tip is a general property of the distal tip components.

Several different designs of sensor guide wires are known in the prior art, and examples of such sensor guide wires are disclosed in U.S. Pat. No. 6,167,763 B1, which describes the cantilevered mounting of the sensor element, U.S. RE39,863 E1, which discloses the sensor element and U.S. Pat. No. 6,248,083 B1, showing the complete sensor guide wire assembly, which all are assigned to the assignee of the present application, and which are hereby all incorporated by reference for the devices and methods described therein.

A presently used sensor wire (the PressureWire™) has proven to fulfill the high requirements regarding torque response. However, the inventors of the present invention have identified a need for a sensor guide wire with further improved torsional rigidity, which thus has a higher polar moment of inertia. There is further a need for a sensor guide wire for which torque response and bending stiffness are optimized to suit the specific needs of each portion of the sensor guide wire.

It is generally known to provide an intravascular medical device with a so-called hypotube to achieve specific properties of the medical device. For example in WO 2009/020961 A1, a medical device for intravascular use comprising a hypotube is disclosed. The object is to provide a medical device which is configured to have a preferential bending direction, which in particular is achieved by providing slots having different widths.

Furthermore, EP 1545680 B1 also discloses a medical device for navigating through the anatomy. The medical device comprises a hypotube provided with slots, wherein the slots may be of unequal size.

In US 2010/0145308 A1, a medical device including an elongated tubing provided with slots in the wall is disclosed. The slots in a group may be unequal in size.

However, these known hypotubes do not possess the required torque response. A further drawback with known hypotubes is that twisting of the hypotube might lead to permanent deformation.

SUMMARY

An object of the present invention is to achieve a sensor guide wire with improved torque response.

A further object of the present invention is to provide a sensor guide wire with improved torque response, while keeping the low bending stiffness, such that the sensor guide wire allows for the same bending radius as the current sensor guide wire.

Still another object of the present invention is to provide a sensor guide wire for which torsion and bending stiffness may be tailored according to specific needs.

The above mentioned objects may be achieved by providing the sensor guide e with a tube making up essentially the entire length of the sensor guide wire, from the proximal end to a distal portion of the sensor guide wire.

According to one aspect of the present invention, the tube may be implemented in any intravascular medical device, such as a sensor guide wire, a guide wire, a catheter or similar device.

In accordance with one embodiment of the present invention, the tube may have a longitudinal extension along a longitudinal axis A, and the tube may comprise a tube wall having a specified thickness. The tube wall may be provided with a plurality of through-going slots, wherein each slot has an essentially elongated shape along a main extension B extending along the circumference of the tube. Each slot has a width W and a length L along the main extension B, and wherein at least two slots are provided in a plane perpendicular to the longitudinal axis A, and the main extension B of the at least two slots are in said plane. A predetermined number of planes with slots may be provided along the tube, and the lengths L of the slots in the same perpendicular plane are essentially the same. The lengths L of the slots in different planes vary along the longitudinal extension of the tube according to a predefined pattern.

The tube according to an embodiment of the present invention can be flexible enough when it comes to bending while keeping much of its torsional rigidity.

By implementing the suggested tube in a sensor guide wire, a higher torsional rigidity can be achieved. The tube can be provided for a sensor guide wire having a higher polar moment of inertia, while keeping the low bending stiffness, such that the sensor guide wire allows for the same bending radius as the presently used wires.

Thus, according to another aspect, the present invention may relate to a sensor guide wire for intravascular measurements of at least one physiological or other variable in a living body.

The sensor guide wire according to one embodiment of the present invention may comprise a tube, the sensor guide wire having a proximal region, a distal sensor region and a tip region. The sensor guide wire may comprise a sensor element arranged in the sensor region, the sensor element comprising a sensor portion, for measuring said variable and to generate a sensor signal in response to said variable. The tube may extend at least partly along said proximal region.

According to yet another aspect of the present invention, the tube may further extend at least partly along the distal sensor region of the sensor guide wire, wherein the tube is adapted to enclose at least a part of the sensor element, and being provided with at least a first sensor opening in the distal sensor region.

The predetermined pattern of the tube may allow an optimized ratio between torsional and bending rigidity.

According to a further aspect, the present invention may relate to a sensor guide wire comprising a tube, which sensor guide wire is "core-wire free," i.e., no core wire is arranged inside and along the tube.

It is to be understood that both the foregoing general description and the following detailed descriptions are exemplary and explanatory only, and are not restrictive of the invention as claimed.

BRIEF DESCRIPTION OF THE DRAWINGS

The features, aspects and advantages of the present invention will become apparent from the following description, appended claims, and the accompanying exemplary embodiments shown in the drawings, which are briefly described below.

FIG. 6 schematically shows a distal portion of a sensor guide wire, the sensor guide wire comprising a tube and a jacket which is arranged in a distal sensor region, according to one embodiment of the present invention.

FIG. 7 schematically shows a distal portion of a sensor guide wire, the sensor guide wire comprising a tube which extends at least partly along the proximal region and further along the distal sensor region, according to one embodiment of the present invention.

FIG. 13 shows a cross-section XIII-XIII of the tube shown in FIG. 10.

FIG. 14 shows a cross-section XIV-XIV of the tube shown in FIG. 10.

FIG. 15 shows a cross-section XV-XV of the tube shown in FIG. 10.

FIG. 16 shows a cross-section XVI-XVI of the tube shown in FIG. 10.

FIG. 17 schematically shows a sensor guide wire according to another embodiment of the present invention.

FIG. 18 schematically shows a first close up view of the sensor guide wire of FIG. 17.

FIG. 19 schematically shows a second close up view of the sensor guide wire of FIG. 17.

FIG. 20 shows a detail I of he tube shown in FIG. 19.

FIG. 21 shows a cross-section XXI-XXI of the tube shown in FIG. 19.

FIG. 22 shows a detail F of the tube shown in FIG. 19.

FIG. 23 shows a cross-section XXIII-XXIII of the tube shown in FIG. 19.

FIG. 24 shows a cross-section XXIV-XXIV of the tube shown in FIG. 19.

FIG. 25 shows a detail G of the tube shown in FIG. 19.

FIG. 26 shows a detail H of the tube shown in FIG. 19.

FIG. 27 shows a cross-section XXVII-XXVII of the tube shown in FIG. 19.

DETAILED DESCRIPTION

Figure 1:
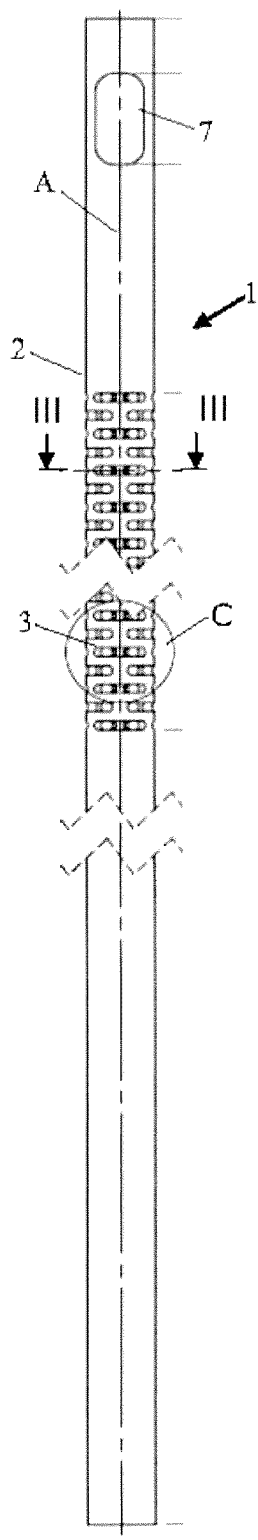
FIG. 1 shows a tube for an intravascular medical device according to one embodiment of the present invention.

With reference to FIG. 1, a tube 1, for an intravascular medical device, according to one embodiment of the present invention, is shown. The tube 1 has a longitudinal extension along a longitudinal axis A, and the tube 1 comprises a tube wall 2 having a specified thickness t (see FIG. 3). The tube wall 2 is provided with a plurality of through-going slots 3. Preferably, the specified thickness t of the tube wall 2 is approximately 0.05 mm. However, the thickness may be between 0.05-2.0 mm. The tube 1 may be provided with a sensor opening 7, as illustrated in FIG. 1. This may be the case when the tube 1 is implemented in a sensor guide wire. However, when the tube 1 is being implemented in, for example, a guide wire or a catheter, the sensor opening 7 may be omitted. In addition, in other embodiments implementing a sensor guide wire, the tube 1 may be provided with additional openings allowing access to the sensor.

Figure 2:
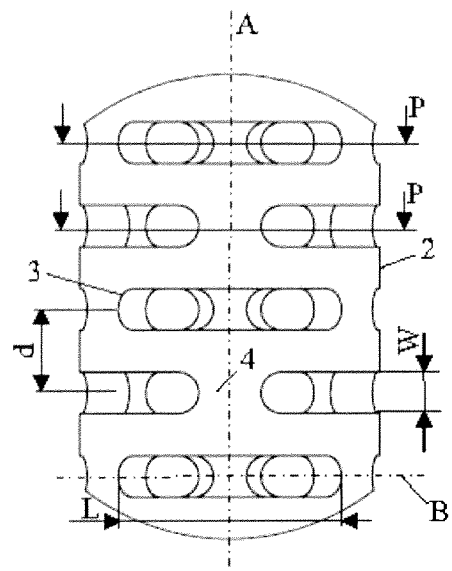
FIG. 2 shows a detail C of the tube shown in FIG. 1.

FIG. 2 shows a detail C of the tube 1 shown in FIG. 1. As illustrated in FIG. 2, each slot 3 has an essentially elongated shape along a main extension B extending along the circumference of the tube 1. Each slot 3 has a width W and a length L along the main extension B. At least two slots 3 are provided in a plane P perpendicular to the longitudinal axis A, the main extension B of the at least two slots 3 being in the plane P. A predetermined number of planes P with slots 3 are provided along the tube 1. Preferably, the width W of a slot 3 is approximately 0.05 mm. However, the width W of a slot 3 may be between 0.05-2.0 mm.

Figure 3:
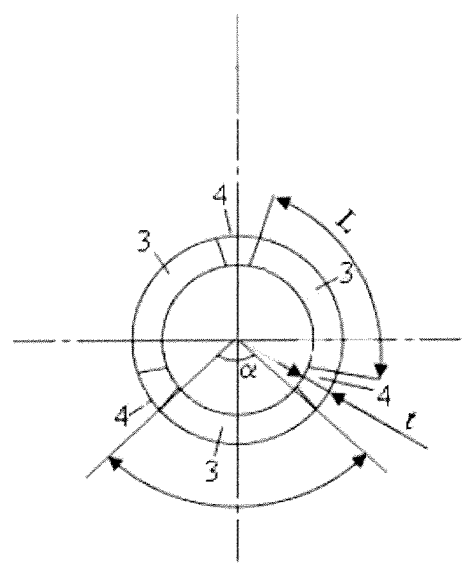
FIG. 3 shows a cross-section of the tube shown in FIG. 1.

In FIG. 3, a cross-section III-III of the tube 1 in FIG. 1 is illustrated. The cross-section illustrates one of the planes P perpendicular to the longitudinal axis A. Three slots 3 are provided in the plane P; however two slots could be used. The slots 3 in the same perpendicular plane P are separated by a slot separation part 4. The lengths L of the slots 3 in the same perpendicular plane P are essentially the same.

As further illustrated in FIG. 3, the slots 3 in the same perpendicular plane P are equally distributed around the circumference of the tube 1. The length L of a slot 3 may be defined by a slot angle $\alpha$, the slot angle being the center angle of the perpendicular plane P. The slot angle is $0° < \alpha < 120°$.

In the embodiment shown in FIG. 3, three equally distributed slots 3 are provided in each plane P. Furthermore, as illustrated in FIG. 2, the slots 3 in a perpendicular plane P are displaced in relation to the slots 3 in an adjacent perpendicular plane P. Preferably, the slots 3 in a perpendicular plane P are displaced approximately 60° with respect to each adjacent perpendicular plane P. However, the degree of displacement may be any angle between 0° and 120°. In case of 0° or 120°, there is no displacement between the slots 3 in the adjacent planes P.

According to another embodiment, four slots 3 may be provided in each perpendicular plane P. In this case, preferably, the slots 3 in a perpendicular plane P are displaced approximately 45° with respect to each adjacent perpendicular plane P. In case of four slots 3 in each plane P, the degree of displacement may be any angle between 0° and 90°. As mentioned above, in case of 0° or 90°, there is no displacement between the slots 3 in the adjacent planes P. Preferably, the degree of displacement is the same between all perpendicular planes P. However, the degree of displacement with respect to an adjacent perpendicular plane P may vary along the tube 1. Preferably, the number of slots 3 provided in each plane P is between 3 and 10.

Figure 4:
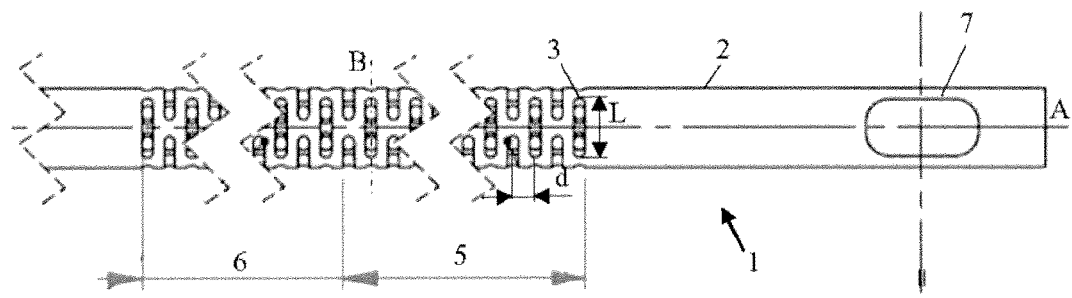
FIG. 4 shows the tube comprising a distal section and a proximal section according to one embodiment of the present invention.

In the embodiment illustrated in FIG. 4, which shows a portion of a tube 1, the lengths L of the slots 3 in different planes P vary along the longitudinal extension of the tube 1, according to a predefined pattern. However, in the drawing, the varying lengths L of the slots 3 can not be seen, this is instead shown in FIG. 5b. FIG. 5b illustrates schematically that the lengths L of the slots 3 in different planes P varies along the longitudinal extension of the tube 1.

According to the predefined pattern shown in FIG. 4, the lengths L of the slots 3 decreases in a proximal direction of the tube 1. The lengths L of the slots 3 may decrease continuously. Furthermore, according to the predefined pattern, the lengths L of the slots 3 are equal in a distal section 5 of the tube 1. As seen in FIG. 4, in the portion of the tube 1 which is proximal to the proximal section 6, no slots are provided in the tube wall 2. However, according to another embodiment, there may be slots provided proximal to the proximal section 6. Preferably, the distal section 5 and the proximal section 6 are arranged adjacent to each other. However, according to another embodiment, there may be an intermediate section (not shown) without slots arranged between the distal section 5 and the proximal section 6. The tube wall 2 may be provided with a sensor opening 7 in a distal portion of the tube 1.

In one embodiment, the length $L_A$, along the longitudinal axis A, of the distal section 5 is approximately 150 mm. The length $L_A$, along the longitudinal axis A, of the proximal section 6 may be approximately 200 mm. However, the length $L_A$ of the distal section 5 may be between 0-3000 mm, and the length of the proximal section 6 may be between 0-3000 mm.

According to one embodiment, the tube 1 is adapted to extend at least partly along the length of a guide wire, a sensor guide wire, or a catheter.

In one embodiment, the tube 1 is provided with a coating covering all, or parts of, the slots. The coating may be made from polyimide, polyurethane, polypropylene, or thermoplastic elastomers, such as a styrene-diene triblock copolymers, polyolefin blend, block copolyurethane, block copoly (ether-ester) and block copoly(ether-amide). In some embodiments, providing the tube 1 with a coating completely covering slots 3 is advantageous in that it prevents ambient fluid, e.g. blood, from entering into the interior of the tube 1. In other embodiments, the coating may provide either a hydrophilic or hydrophobic outer surface, to optimize the frictional forces between the outer surface of the tube 1 and e.g. the vessel wall or a catheter. This can be accomplished by choosing a material with proper hydrophilic/hydrophobic properties or by surface modification and/or treatment of abovementioned polymeric coating materials.

As illustrated in FIGS. 2 and 4, adjacent perpendicular planes P are separated by a predetermined separation distance d, being approximately 0.1 mm (see also FIG. 2). However, the distance d may be between 0.05-4.0 mm. According to one embodiment, the predetermined number of perpendicular planes P is between 1000-10000, preferably the predetermined number of planes P is in the interval 1000-5000, and more preferably the predetermined number of planes P is approximately 3500.

Figure 5A:
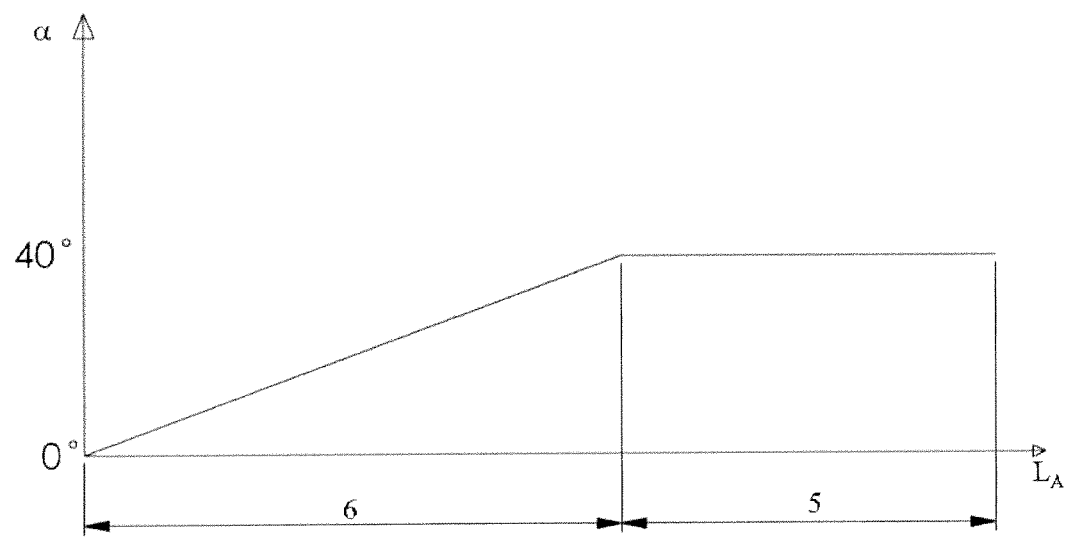
FIG. 5a shows a diagram which illustrates how the slot angle varies in the distal section and the proximal section, according to one embodiment of the present invention.
Figure 5B:
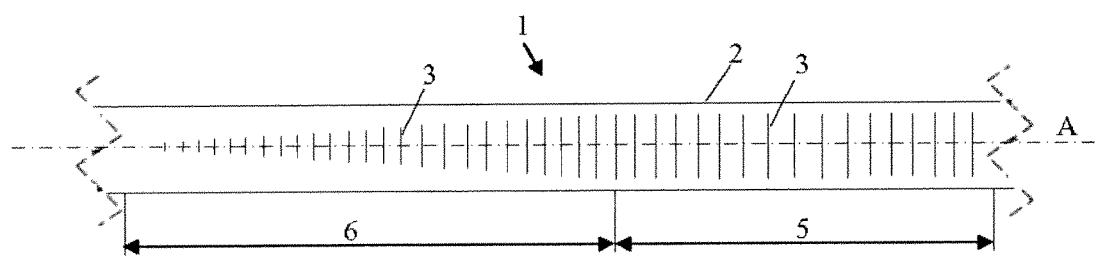
FIG. 5b shows schematically that the lengths of the slots decreases continuously along the proximal section and that the lengths of the slots are equal along the distal section, according to one embodiment of the present invention.

According to one embodiment, as illustrated by the diagram shown in FIG. 5a, the lengths L of the slots 3 decreases continuously. The slot angle $\alpha$ decreases from approximately 40° to approximately 0°, i.e. no slots, in a proximal section 6 of the tube 1, and the slot angle $\alpha$ is approximately 40° in the distal section 5 of the tube 1.

In one embodiment, the tube 1 has an inner diameter of approximately 0.25 mm, and an outer diameter of approximately 0.35 mm.

In FIG. 5b the proximal section 6 and the distal section 5 are schematically shown. In FIG. 5b, some slots 3 have been omitted for sake of simplicity. As mentioned above, FIG. 5b schematically illustrates that the lengths L of the slots 3 decreases continuously along the proximal section 6 and the lengths L of the slots 3 are equal, or essentially equal, along the distal section 5, according to one embodiment of the present invention.

FIG. 6 illustrates a sensor guide wire 8 for intravascular measurements of at least one physiological or other variable in a living body, comprising a tube 1 as described herein. In the embodiment shown in FIG. 6, the sensor guide wire 8 has a proximal region 9, a distal sensor region 10 and a tip region 11. The sensor guide wire 8 comprises a sensor element 12 arranged in the sensor region 10, and comprising a sensor portion 13, for measuring the variable and to generate a sensor signal in response to the variable. The tube 1 extends at least partly along the proximal region 9 of the sensor guide wire 8. The sensor guide wire 8 comprising a tube 1 as described herein achieves all requirements set up for the sensor guide wire 8, the sensor guide wire 8 provides an optimized ratio between torsional and bending rigidity.

As illustrated in FIG. 6, the tube 1 extends at least partly along the proximal region 9. Furthermore, the sensor guide wire 8 is provided with a jacket 15 enclosing at least a portion of the sensor element 12. The jacket 15 extends along the distal sensor region 10. The jacket 15 is further provided with at least a first sensor opening 7 in the distal sensor region 10. The jacket 15 may be provided with additional openings allowing access to the sensor element 12. Preferably, the proximal end 16 of the jacket 15 is attached to a distal end 17 of the tube 1. In another embodiment, the tube 1 may extend along the proximal region 9 and further in at least parts of the distal sensor region 10.

In the embodiment shown in FIG. 7, the sensor guide wire 8 has a proximal region 9, a distal sensor region 10 and a tip region 11. The sensor guide wire 8 comprises a sensor element 12 arranged in the sensor region 10, and comprising a sensor portion 13, for measuring the variable and to generate a sensor signal in response to the variable. The tube 1 extends at least partly along the proximal region 9. The tube 1 further extends along the distal sensor region 10, and is adapted to enclose at least a part of the sensor element 12. The tube 1 is provided with at least a first sensor opening 7 in the distal sensor region 10.

Thus, according to one embodiment, as illustrated in FIG. 7, the tube 1 runs along the proximal region 9 and the entire distal sensor region 10, such that the sensor region 10 is an integrated part of the tube 1.

In one embodiment, no core wire is arranged to extend along the proximal region 9. In another embodiment, no core wire is arranged to extend along the distal sensor region 10. In yet another embodiment, no core wire is arranged to extend along the proximal region 9 and the distal sensor region 10. Accordingly, the sensor guide wire 8 may be core wire free, wherein the tube 1 provides the same properties as a core wire. A security string (not shown) may extend from a proximal end (not shown) to a distal end 14, or at least to the tip region 11, of the sensor guide wire 8. The security string may be a flexible wire running inside the tube 1.

Preferably, the security string is embodied by a relatively thin flexible wire. The security string may be attached, at its distal end to e.g. a distal part of the sensor guide wire 8. Preferably, the security string is attached essentially at the distal end 14, or to a tip core wire (not shown) running along the tip region 11 of the sensor guide wire 8. The reason for arranging such a security string is to ensure all parts are held together by the string. However, in another embodiment, the sensor guide wire 8 may be provided with a core wire running inside and along the tube 1.

According to the embodiments shown in FIGS. 6-7, the distal section 5 and the proximal section 6 of the tube 1 are arranged in the proximal region 9 of the sensor guide wire 8.

Figure 8:
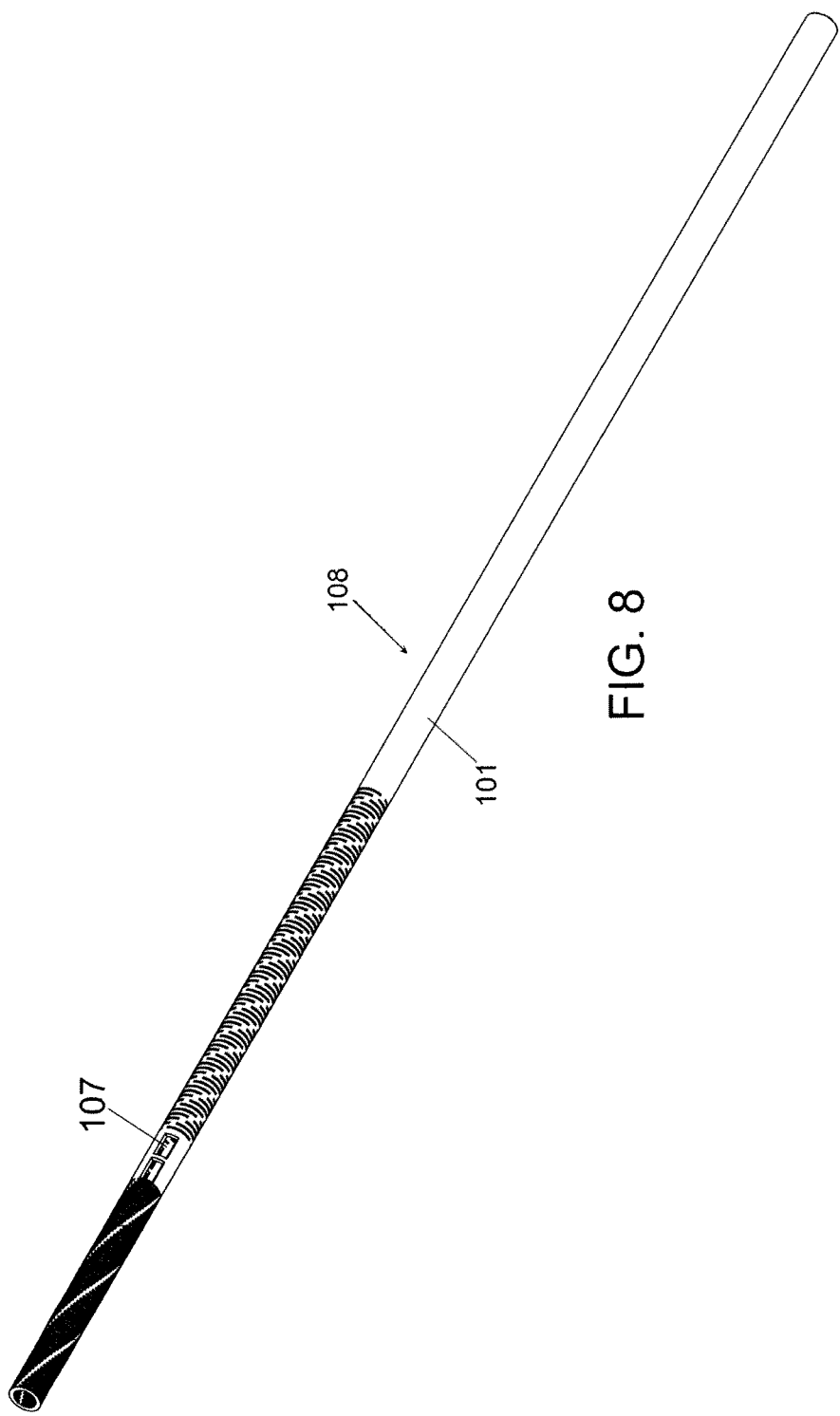
FIG. 8 schematically shows a sensor guide wire according to another embodiment of the present invention.
Figure 9:
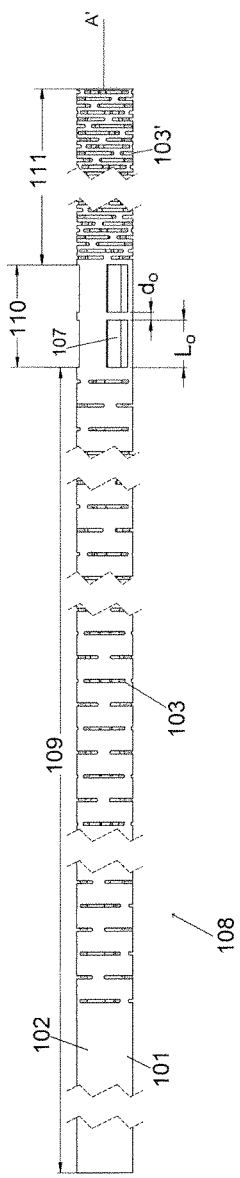
FIG. 9 schematically shows a first close up view of the sensor guide wire of FIG. 8.
Figure 10:
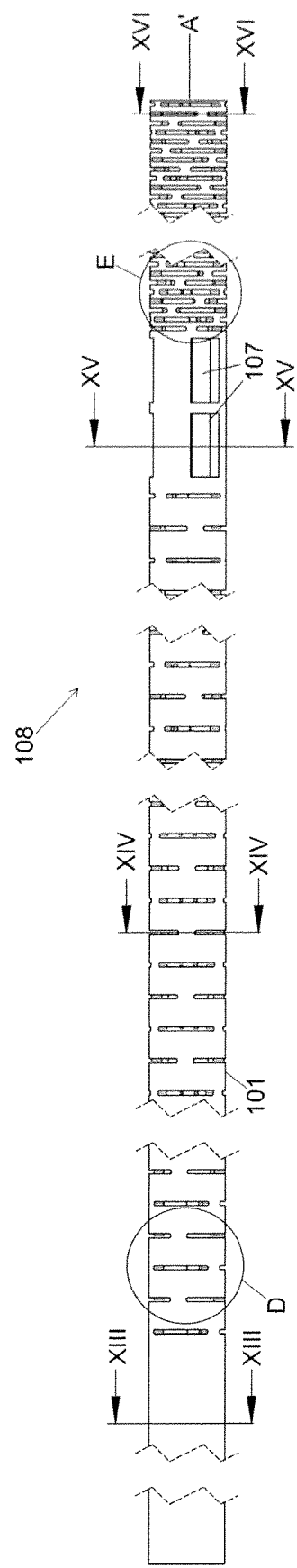
FIG. 10 schematically shows a second close up view of the sensor guide wire of FIG. 8.

FIGS. 8-10 illustrate a sensor guide wire 108 for an intravascular measurement of at least one physiological or other variable in a living body, comprising a tube 101. The sensor guide wire 108 has a proximal region 109, a distal sensor region 110 and a tip region 111. The sensor guide wire 108 comprises a sensor element arranged in the sensor region 110, and comprising a sensor portion for measuring the variable and to generate a sensor signal in response to the variable. The tube 101 extends at along the proximal region 109, the entire distal sensor region 110, and the tip region 111 of the sensor guide wire 108. Thus, according to the embodiment in FIGS. 8-10, the tube 101 runs along the proximal region 109, the entire distal sensor region 110, and the tip region 111 such that the sensor region 110 and the tip region 111 are an integrated part of the tube 101.

The distal sensor region 110 is further provided with at least a first sensor opening 107. The distal sensor region 110 may be provided with additional openings 107 allowing access to the sensor element 12. As seen in FIGS. 10 and 15, there may be three openings at two different locations along the longitudinal axis of the distal sensor region 110.

In one embodiment, no core wire is arranged to extend along the proximal region 109. In another embodiment, no core wire is arranged to extend along the distal sensor region 110. In yet another embodiment, no core wire is arranged to extend along the proximal region 109 and the distal sensor region 110. Accordingly, the sensor guide wire 108 may be core wire free, wherein the tube 101 provides the same properties as a core wire. A security string (not shown) may extend from a proximal end (not shown) to a distal end, or at least to the tip region 111, of the sensor guide wire 108. The security string may be a flexible wire running inside the tube 101.

Preferably, the security string is embodied by a relatively thin flexible wire. The security string may be attached, at its distal end to e.g. a distal part of the sensor guide wire 108. Preferably, the security string is attached essentially at the distal end of the senor guide wire 108. However, in another embodiment, the sensor guide wire 108 may be provided with a core wire running inside and along the tube 101.

With reference to FIGS. 9, 10, and 13, the tube 101 has a longitudinal extension along a longitudinal axis A', and the tube 101 comprises a tube wall 102 having a specified thickness t'. Preferably, the specified thickness t' of the tube wall 102 is approximately 0.05 mm. However, the thickness may be between 0.02-2.0 mm. The tube 101 may be provided with the sensor opening 107, as illustrated in FIGS. 8-10. This may be the case when the tube 101 is implemented in a sensor guide wire. However, when the tube 101 is being implemented in, for example a guide wire or a catheter, the sensor opening 107 may be omitted. In addition, the tube 101 is provided with additional openings 107 allowing access to the sensor, but these additional openings 107 may be omitted.

In FIG. 15, a cross-section XV-XV of the tube 101 in FIG. 10 illustrates one of the planes perpendicular to the longitudinal axis in the distal sensor region 110 with openings 107. Three openings 107 are provided in the plane. The openings 107 in the same perpendicular plane P' are separated by a slot separation part 120. The lengths of the openings 107 in the same perpendicular plane are essentially the same. The openings 107 in the same perpendicular plane P' are equally distributed around the circumference of the tube 101. The length of an opening 107 may be defined by a slot angle α''', the slot angle being the center angle of the perpendicular plane. The slot angle is 0°<α'''<120°, preferably about 50°. In the embodiment shown in FIG. 15, three equally distributed openings 107 are provided in each plane. The length $L_o$ of each opening 107 may be any suitable length, such as for example between 0.25 to 2 mm, preferably 0.7 mm. Also the distance $d_o$ between adjacent openings in the longitudinal axis may be any suitable distance, such as for example 0.1 to 1 mm, preferably 0.4 mm.

Figure 11:
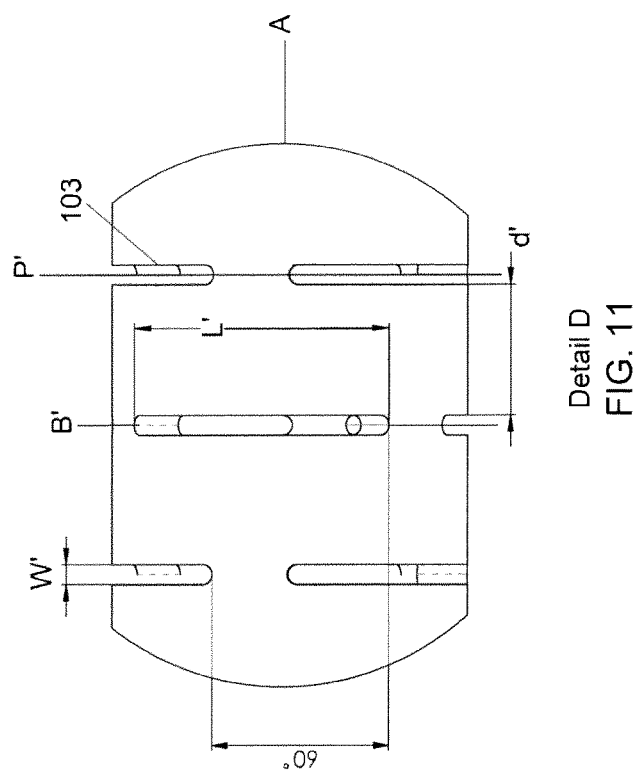
FIG. 11 shows a detail D of the tube shown in FIG. 10.

FIG. 11 shows a detail D of the tube 101 shown in FIG. 10. As illustrated in FIG. 11, each slot 103 has an essentially elongated shape along a main extension B' extending along the circumference of the tube 101. Each slot 103 has a width W' and a length L' along the main extension B'. At least two slots 103 are provided in a plane P' perpendicular to the longitudinal axis A', the main extension B' of the at least two slots 103 being in the plane P'. A predetermined number of planes P' with slots 103 are provided along the tube 101. Preferably, the width W' of a slot 103 is approximately 0.02 mm. However, the width W' of a slot 103 may be between 0.01-2.0 mm.

In FIG. 13, a cross-section XIII-XIII of the tube 101 in FIG. 10 is illustrated at the proximal region 109 with no slots. In FIG. 14, the cross-section XIV-XIV illustrates one of the planes P' perpendicular to the longitudinal axis A' in the proximal region 109 with slots. Three slots 103 are provided in the plane P'; however, two slots may be used instead. The slots 103 in the same perpendicular plane P are separated by a slot separation part 104. The lengths L' of the slots 103 in the same perpendicular plane P' are essentially the same. As further illustrated in FIG. 14, the slots 103 in the same perpendicular plane P' are equally distributed around the circumference of the tube 101. The length L' of a slot 103 may be defined by a slot angle α', the slot angle being the center angle of the perpendicular plane P'. The slot angle is 0°<α'<160°, preferably about 95°.

In the embodiment shown in FIG. 14, three equally distributed slots 103 are provided in each plane P'; however, two slots could be used instead. Furthermore, as illustrated in FIG. 11, the slots 103 in a perpendicular plane P' are displaced in relation to the slots 103 in an adjacent perpendicular plane P'. Preferably, the slots 103 in a perpendicular plane P' are displaced approximately 60° with respect to each adjacent perpendicular plane P'. However, the degree of displacement may be any angle between 0° and 120°.

As illustrated in FIG. 11, adjacent perpendicular planes P' are separated by a predetermined separation distance d', being approximately 0.04 mm. However, the distance d' may be between 0.01-4.0 mm. According to one embodiment, the predetermined number of perpendicular planes P is between 1000-10000, preferably the predetermined number of planes P is in the interval 1000-5000, and more preferably the predetermined number of planes P is approximately 3500.

Figure 12:
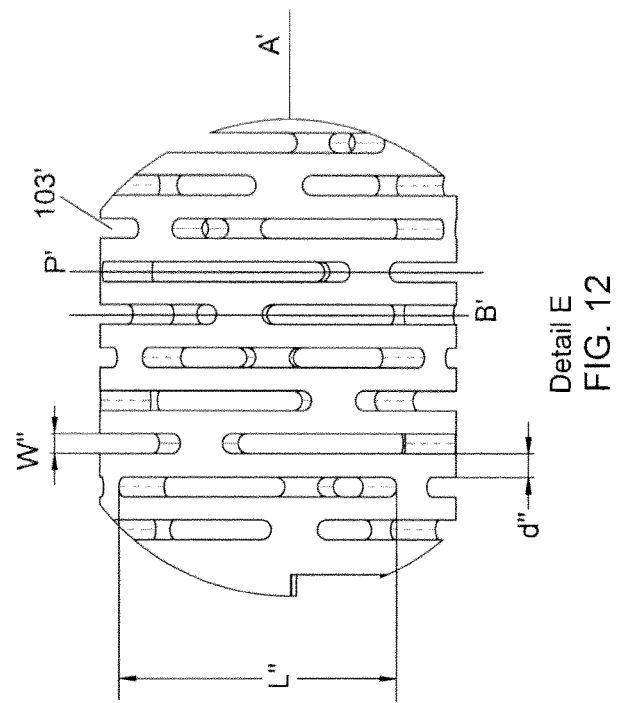
FIG. 12 shows a detail E of the tube shown in FIG. 10.

The tube 101 may be provided with a plurality of slots. FIG. 12 shows a detail E of the tube 101 shown in FIG. 10. As illustrated in FIG. 12, each slot 103' has an essentially elongated shape along the main extension B' extending along the circumference of the tube 101. Each slot 103' has a width W'' and a length L'' along the main extension B'. At least two slots 103' are provided in a plane P' perpendicular to the longitudinal axis A', the main extension B' of the at least two slots 103' being in the plane P'. A predetermined number of planes P' with slots 103' are provided along the tube 101. Preferably, the width W'' of a slot 103' is approximately 0.02 mm. However, the width W' of a slot 103' may be between 0.01-2.0 mm.

In FIG. 16, a cross-section XVI-XVI of the tube 101 in FIG. 10 illustrates one of the planes P' perpendicular to the longitudinal axis A' in the tip region 111 with slots. Three slots 103' are provided in the plane P'; however two slots could be used instead. The slots 103' in the same perpendicular plane P' are separated by a slot separation part 104'. The lengths L'' of the slots 103 in the same perpendicular plane P' are essentially the same. As further illustrated in FIG. 16, the slots 103' in the same perpendicular plane P' are equally distributed around the circumference of the tube 101. The length L'' of a slot 103' may be defined by a slot angle α'', the slot angle being the center angle of the perpendicular plane P'. The slot angle is 0°<α'<160°, preferably about 105°. Furthermore, as illustrated in FIG. 12, the slots 103' in a perpendicular plane P' are displaced in relation to the slots 103' in an adjacent perpendicular plane P'. The degree of displacement may be any angle between 0° and 120°.

As illustrated in FIG. 12, adjacent perpendicular planes P' are separated by a predetermined separation distance d'', being approximately 0.02 mm. However, the distance d''' may be between 0.01-4.0 mm. According to one embodiment, the predetermined number of perpendicular planes P is between 1000-10000, preferably the predetermined number of planes P is in the interval 1000-5000, and more preferably the predetermined number of planes P is approximately 3500.

In the embodiment of FIGS. 8-10, the tube 101 may optionally be provided with a coating covering all, or parts of, the slots 103 and 103'. The coating may be made from polyimide, polyurethane, polypropylene, or thermoplastic elastomers, such as a styrene-diene triblock copolymers, polyolefin blend, block copolyurethane, block copoly(ether-ester) and block copoly(ether-amide). In some embodiments, providing the tube 101 with a coating completely covering slots 103 and 103' is advantageous in that it prevents ambient fluid, e.g. blood, from entering into the interior of the tube 101. In other embodiments, the coating may provide either a hydrophilic or hydrophobic outer surface, to optimize the frictional forces between the outer surface of the tube 101 and e.g. the vessel wall or a catheter. This can be accomplished by choosing a material with proper hydrophilic/hydrophobic properties or by surface modification and/or treatment of abovementioned polymeric coating materials.

FIGS. 17-19 illustrate a sensor guide wire 208 for an intravascular measurement of at least one physiological or other variable in a living body, comprising a tube 201. The embodiment of FIGS. 17-19 is a variation of the embodiment in FIGS. 8-10 with some differences, for example, the angle of displacement for the slots in the proximal region of FIG. 22 is 10° instead of 60° (as shown in the proximal region of FIG. 11). In the embodiment shown in FIGS. 17-19, the sensor guide wire 208 has a proximal region 209, a distal sensor region 210 and a tip region 211. The sensor guide wire 208 comprises a sensor element arranged in the sensor region 210, and comprising a sensor portion for measuring the variable and to generate a sensor signal in response to the variable. The tube 201 extends at along the proximal region 209, the entire distal sensor region 210, and the tip region 211 of the sensor guide wire 208. Thus, according to the embodiment in FIGS. 17-19 and 23, the tube 201 runs along the proximal region 209, the entire distal sensor region 210, and the tip region 211 such that the sensor region 210 and the tip region 211 are an integrated part of the tube 201.

The distal sensor region 210 is further provided with at least a first sensor opening 207. The distal sensor region 210 may be provided with additional openings 207 allowing access to the sensor element. As seen in FIGS. 17-19, there may be three openings at two different locations along the longitudinal axis of the distal sensor region 210.

In one embodiment, no core wire is arranged to extend along the proximal region 209. In another embodiment, no core wire is arranged to extend along the distal sensor region 210. In yet another embodiment, no core wire is arranged to extend along the proximal region 209 and the distal sensor region 210. Accordingly, the sensor guide wire 208 may be core wire free, wherein the tube 201 provides the same properties as a core wire. A security string (not shown) may extend from a proximal end (not shown) to a distal end, or at least to the tip region 211, of the sensor guide wire 208. The security string may be a flexible wire running inside the tube 201.

Preferably, the security string is embodied by a relatively thin flexible wire. The security string may be attached, at its distal end to e.g. a distal part of the sensor guide wire 208. Preferably, the security string is attached essentially at the distal end of the senor guide wire 208. However, in another embodiment, the sensor guide wire 208 may be provided with a core wire running inside and along the tube 201.

With reference to FIGS. 18, 19, and 21, the tube 201 has a longitudinal extension along a longitudinal axis $A_1$, and the tube 201 comprises a tube wall 202 having a specified thickness $t_1$. Preferably, the specified thickness $t_1$ of the tube wall 202 is approximately 0.05 mm. However, the thickness may be between 0.02-2.0 mm. The tube 201 may be provided with the sensor opening 207, as illustrated in FIGS. 17-19. This may be the case when the tube 201 is implemented in a sensor guide wire. However, when the tube 201 is being implemented in, for example a guide wire or a catheter, the sensor opening 207 may be omitted. In addition, the tube 201 is provided with additional openings 207 allowing access to the sensor, but these additional openings 207 may be omitted.

In FIG. 23, a cross-section XXIII-XXIII of the tube 201 in FIG. 19 illustrates one of the planes perpendicular to the longitudinal axis in the distal sensor region 210 with openings 207. Three openings 207 are provided in the plane $P_1$. The openings 207 in the same perpendicular plane $P_1$ are separated by a slot separation part 220. The lengths of the openings 207 in the same perpendicular plane are essentially the same. As further illustrated in FIG. 23, the openings 207 in the same perpendicular plane $P_1$ are equally distributed around the circumference of the tube 201. The length of an opening 207 may be defined by a slot angle $\alpha_1$, the slot angle being the center angle of the perpendicular plane. The slot angle is $0°<\alpha_1<120°$, preferably about 50°. In the embodiment shown in FIG. 23, three equally distributed openings 207 are provided in each plane. The length $L_1$ of each opening 207 may be any suitable length, such as for example between 0.25 to 2 mm, preferably 0.7 mm. Also the distance $d_1$ between adjacent openings in the longitudinal axis may be any suitable distance, such as for example 0.1 to 1 mm, preferably 0.4 mm.

The tube 201 may be provided with a plurality of slots. FIG. 22 shows a detail F of the tube 201 shown in FIG. 19. As illustrated in FIG. 22, each slot 203 has an essentially elongated shape along a main extension $B_1$ extending along the circumference of the tube 201. Each slot 203 has a width $W_1$ and a length $L_1$ along the main extension $B_1$. At least two slots 203 are provided in a plane $P_1$ perpendicular to the longitudinal axis $A_1$, the main extension $B_1$ of the at least two slots 203 being in the plane $P_1$. A predetermined number of planes $P_1$ with slots 203 are provided along the tube 201. Preferably, the width $W_1$ of a slot 203 is approximately 0.04 mm. However, the width $W_1$ of a slot 203 may be between 0.01-2.0 mm.

In FIG. 21, a cross-section XXI-XXI of the tube 201 in FIG. 19 is illustrated at the proximal region 209 with no slots. In FIG. 24, the cross-section XXIV-XXIV illustrates one of the planes $P_1$ perpendicular to the longitudinal axis $A_1$ in the proximal region 209 with slots. Three slots 203 are provided in the plane $P_1$; however two slot would be used instead. The slots 203 in the same perpendicular plane $P_1$ are separated by a slot separation part 204. The lengths of the slots 203 in the same perpendicular plane $P_1$ are essentially the same. As further illustrated in FIG. 24, the slots 203 in the same perpendicular plane $P_1$ are equally distributed around the circumference of the tube 201. The length of a slot 203 may be defined by a slot angle $\alpha_2$, the slot angle being the center angle of the perpendicular plane $P_1$. The slot angle is $0°<\alpha_2<160°$, preferably about 95°.

In FIG. 24, three equally distributed slots 203 are provided in each plane $P_1$. Furthermore, as illustrated in FIG. 22, the slots 203 in a perpendicular plane $P_1$ are displaced in relation to the slots 203 in an adjacent perpendicular plane $P_1$. Preferably, the slots 203 in a perpendicular plane $P_1$ are displaced approximately 10° with respect to each adjacent perpendicular plane $P_1$. However, the degree of displacement may be any angle between 0° and 120°.

As illustrated in FIGS. 22 and 25, adjacent perpendicular planes $P_1$ are separated by a predetermined separation distance. For example, in the segment $S_1$ of the proximal region 209, the separation distance $d_2$ between adjacent perpendicular planes may be a constant value, such as a value between about 0.10 mm and about 4.0 mm, preferable about 0.18 mm or 0.14 mm. In segment $S_2$ of the proximal region 209, the separation distance between adjacent perpendicular planes decrease in a linear fashion from the constant value $d_2$ down to a lower value $d_3$. The separation distance $d_3$ may be a value between about 0.10 mm and about 0.01 mm, preferably about 0.025 mm. The lengths of segments $S_1$ and $S_2$ may be any sub-portion of the proximal region 209. For example, the combined length of segments $S_1$ and $S_2$ may be between about 100 mm to about 1000 mm, preferably 290 mm, The ratio of the length of $S_2$ relative to $S_1$ may be any suitable ratio, such as, for example, 0, 0.1, 0.2, 0.3, 0.4, 0.5, 0.6, 0.7 0.8, 0.9, or 1 or any value therebetween. Alternatively, the ratio of the length of $S_1$ relative to $S_2$ may be any suitable ratio, such as, for example, 0, 0.1, 0.2, 0.3, 0.4, 0.5, 0.6, 0.7 0.8, 0.9, or 1 or any value therebetween. According to another embodiment, as seen in FIG. 25, a number of adjacent perpendicular planes at the end portion of the proximal region 209 nearest the distal sensor region 210 may be at the constant distance $d_3$ from each other. For example, one, two, three, four, twenty, fifty, or more or any integer in-between of the adjacent perpendicular planes at the end portion of the proximal region 209 nearest the distal sensor region 210 may have a separation distance from their adjacent perpendicular planes at the lower value $d_3$. According to one embodiment, the predetermined number of perpendicular planes $P_1$ is between 1000-10000, preferably the predetermined number of planes $P_1$ is in the interval 1000-5000, and more preferably the predetermined number of planes $P_1$ is approximately 3500.

FIG. 26 shows a detail H of the tube 201 shown in FIG. 19. As illustrated in FIG. 26, each slot 203' has an essentially elongated shape along the main extension $B_1$ extending along the circumference of the tube 201. Each slot 203' has a width $W_2$ and a length $L_2$ along the main extension $B_1$. At least two slots 203' are provided in a plane $P_1$ perpendicular to the longitudinal axis $A_1$, the main extension $B_1$ of the at least two slots 203' being in the plane $P_1$. A predetermined number of planes $P_1$ with slots 203' are provided along the tube 201. Preferably, the width $W_2$ of a slot 203 is approximately 0.04 mm. However, the width $W_2$ of a slot 203 may be between 0.01-2.0 mm.

In FIG. 27, a cross-section XXVII-XXVII of the tube 201 in FIG. 19 illustrates one of the planes $P_1$ perpendicular to the longitudinal axis $A_1$ in the tip region 211 with slots. Three slots 203' are provided in the plane $P_1$; however two slots could be used instead. The slots 203' in the same perpendicular plane $P_1$ are separated by a slot separation part 204'. The lengths $L_2$ of the slots 203' in the same perpendicular plane $P_1$ are essentially the same. As further illustrated in FIG. 27, the slots 203' in the same perpendicular plane $P_1$ are equally distributed around the circumference of the tube 201. The length $L_2$ of a slot 203' may be defined by a slot angle $\alpha_3$, the slot angle being the center angle of the perpendicular plane $P_1$. The slot angle is $0° < \alpha_3 < 160°$, preferably about 105°. In FIGS. 20 and 27, three equally distributed slots 203' are provided in each plane $P_1$. Furthermore, as illustrated in FIG. 26, the slots 203' in a perpendicular plane $P_1$ are displaced in relation to the slots 203' in an adjacent perpendicular plane $P_1$. The degree of displacement may be any angle between 0° and 120°.

As illustrated in FIGS. 26 and 20, adjacent perpendicular planes $P_1$ are separated by a predetermined separation distance. For example, the separation distance $d_4$ between adjacent perpendicular planes in FIG. 26 may be a constant value, such as a value between about 0.01 mm and about 4.0 mm, preferable about 0.03 mm. The separation distance $d_5$ in FIG. 20 may be a value between about 0.01 mm and about 4.0 mm, preferably about 0.025 mm. The separation distance between adjacent perpendicular planes may vary such that it decreases (for example, in a linear or other fashion) from the value $d_4$ at the proximal end portion of the tip region 211 down to the lower value $d_5$ at the distal end portion of the tip region 211. According to another embodiment, a number of adjacent perpendicular planes at either the proximal or distal end portion of the tip region 211 may be at a constant separation distance from each other. For example, one, two, three, four, twenty, fifty, or more or any integer in-between of the adjacent perpendicular planes at the proximal end portion of the tip region 211 nearest the distal sensor region 210 may have a separation distance from their adjacent perpendicular planes at the higher value $d_4$. Alternatively or additionally, one, two, three, four, twenty, fifty, or more or any integer in-between of the adjacent perpendicular planes at the distal end portion of the tip region 211 farthest from the distal sensor region 210 may have a separation distance from their adjacent perpendicular planes at the lower value $d_5$. According to one embodiment, the predetermined number of perpendicular planes $P_1$ is between 1000-10000, preferably the predetermined number of planes $P_1$ is in the interval 1000-5000, and more preferably the predetermined number of planes $P_1$ is approximately 3500.

In the embodiment of FIGS. 17-19, the tube 201 may be optionally provided with a coating covering all, or parts of, the slots 203 and 203'. The coating may be made from polyimide, polyurethane, polypropylene, or thermoplastic elastomers, such as a styrene-diene triblock copolymers, polyolefin blend, block copolyurethane, block copoly(ether-ester) and block copoly(ether-amide). In some embodiments, providing the tube 201 with a coating completely covering slots 203 and 203' is advantageous in that it prevents ambient fluid, e.g. blood, from entering into the interior of the tube 201. In other embodiments, the coating may provide either a hydrophilic or hydrophobic outer surface, to optimize the frictional forces between the outer surface of the tube 201 and e.g. the vessel wall or a catheter. This can be accomplished by choosing a material with proper hydrophilic/hydrophobic properties or by surface modification and/or treatment of abovementioned polymeric coating materials.

According to other embodiments, the proximal regions 9, 109, and 209 may be exchanged for one another among the embodiments of FIGS. 1-27; the distal sensor regions 10, 110, and 210 may be exchanged for one another among the embodiments of FIGS. 1-27, the tip regions 11, 111, and 211 may be exchanged for one another among the embodiments of FIGS. 1-27, or any combination of the proximal regions, distal sensor regions, and tip regions in FIGS. 1-27 may be used.

The tube 1, 101, 201 according to any of the above embodiments may be produced by providing an elongated sheet material, e.g. made from steel or nitinol, which is subsequently bent or shaped into an essentially cylindrical elongated tube 1, 101, 201. The slots may be provided in the sheet material prior to shaping the sheet material 1, 101, 201 into a tube 1, 101, 201 or after the sheet material has been shaped into a tube 1, 101, 201. The slots may be provided by laser cutting, etching, grinding or by using any other technique suitable to provide slots in the sheet material or the elongated tube 1, 101, 201. The predetermined pattern in the tube 1, 101, 201 may for example be provided by photoetching, which is a process wherein photographic pattern transfer and etch technique are combined.

According to another embodiment of the present invention, a guide wire and sensor assembly may have an overall distal section of around 320 mm having a slot design for enhanced functionality of the assembly. The overall distal section of this embodiment having the slot design would include a semi-flexible section of around 290 mm (as a distal portion of the proximal region having the slots), a 2.12 mm sensor jacket housing (as the distal sensor region) and a 30 mm tip section (as the tip region). The slot size (width and/or width), the number of slots in a cross section, the slot cut angle and the distance between slots will be changed to suit the required stiffness and flexibility of the distal section of the assembly. This embodiment would contain combination of either two and three slots or only two slots or only three slots along the overall distal section except in the sensor jacket housing. The sensor jacket housing section may include 1-6 slots in a cross section. The slot width would be anything between 0.01 mm and 0.1 mm and the slot cut angle would be between 70° and 160° along the overall distal section having the slot design except in the sensor jacket housing. The angle typically is more relevant to laser cutting process. However when another slot making process is used, the slot circumferential length should be equal to what is defined in the laser processing. The sensor jacket housing would include slots with a width between 0.005 mm and 2 mm and a cut angle between 5° and 180°. The slot position will be rotated along the tube to have predetermined minimum directional properties along the wire. This rotation angle may be in between 0°-180°. A suitable material for this embodiment would be linear or super elastic nitinol, all type of steel and any metal/alloy whose Young Modulus lies between 50 GPa and 250 GPa. A shape memory properties may be incorporated in the 30 mm tip section by a suitable heat treatment process. The creation of the cut/slots is not limited to a laser cutting process, but any other process creating cut such as etching, EDM and machining could be used. Flexibility, torqucability and tip floppiness are important properties of the guide wire assembly during PCI procedure while the conventional ways to design a guide wire assembly tip with solid metals or material such as stainless steel does not have much freedom to change stiffness along the wire. These conventional designs would also include several parts glued or mechanically joined together.

For this embodiment, as the flexibility is changed smoothly along the length of the guide wire, friction against the wall will be less, especially in a complex tortuous path, as the bending force against the wall is less. Since the friction is minimized, torque transfer will be improved. Since this embodiment may include a sensor jacket housing and a flexible tip as a single unitary one-piece component without any joint, it possibly eliminates potential torque absorbing points as well as weak mechanical joints. Since this embodiment can include a flexible slotted tip design, there is a possibility to use radioopaque polymer inside the tube.

Figure 28:
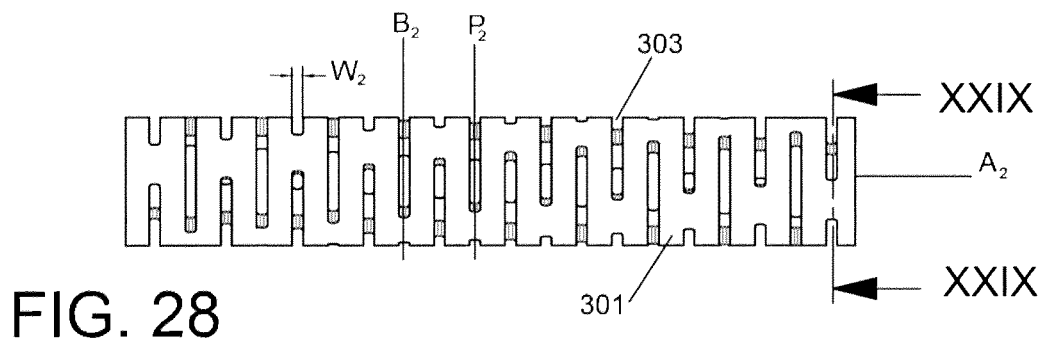
FIG. 28 shows a section of tube according to another embodiment of the present invention.

FIGS. 27 and 28 show a section of a tube 301 according to an embodiment of the present invention. The tube section may be provided with a plurality of slots 303. Each slot 303 has an essentially elongated shape along a main extension $B_2$ extending along the circumference of the tube section 301. Each slot 303 has a width $W_3$ and a length along the main extension $B_2$. At least two slots 303 are provided in a plane $P_2$ perpendicular to the longitudinal axis $A_2$, the main extension $B_2$ of the at least two slots 303 being in the plane $P_2$. A predetermined number of planes $P_2$ with slots 303 are provided along the tube section 301. Preferably, the width $W_2$ of a slot 303 may be between 0.01-2.0 mm.

Figure 29:
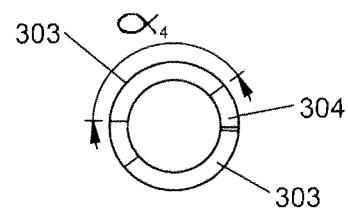
FIG. 29 shows a cross-section XXIX-XXIX of the tube section shown in FIG. 29.

In FIG. 29, the cross-section XXIX-XXIX illustrates one of the planes $P_2$ perpendicular to the longitudinal axis $A_2$. Two slots 303 are provided in the plane $P_1$. The slots 303 in the same perpendicular plane $P_2$ are separated by a slot separation part 304. The lengths of the slots 303 in the same perpendicular plane $P_2$ are essentially the same, and are equally distributed around the circumference of the tube section 301. The length of a slot 303 may be defined by a slot angle $\alpha_4$, the slot angle being the center angle of the perpendicular plane $P_2$. The slot angle is $0°<\alpha_4<160°$, preferably about 142.5°.

In FIG. 29, two equally distributed slots 303 are provided in each plane $P_2$. Furthermore, as illustrated in FIG. 28, the slots 303 in a perpendicular plane $P_2$ are displaced in relation to the slots 303 in an adjacent perpendicular plane $P_2$. The slots 303 in a perpendicular plane $P_2$ are displaced approximately 10° or 60° with respect to each adjacent perpendicular plane $P_1$. However, the degree of displacement may be any angle between 0° and 120°.

The tube section 303 may be used as a section of a tube in any of the previously-mentioned embodiments. For example, the tube section 303 may be used in place of the section of tube in the proximal region 109 in FIG. 9, the tip region 111 in FIG. 9, the proximal region 209 in FIG. 18, or the tip region 211 in FIG. 18.

Besides those embodiments depicted in the figures and described in the above description, other embodiments of the present invention are also contemplated. For example, any single feature of one embodiment of the present invention may be used in any other embodiment of the present invention. For example, the following is a list of embodiments, but the invention should not be viewed as being limited to these embodiments.

(I) A tube (1) for an intravascular medical device, said tube (1) having a longitudinal extension along a longitudinal axis A, and that said tube (1) comprising a tube wall (2) having a specified thickness t, and being provided with a plurality of through-going slots (3), wherein each slot (3) has an essentially elongated shape along a main extension B extending along the circumference of said tube (1), wherein each slot (3) has a width W and a length L along said main extension B, and wherein at least two slots (3) are provided in a plane P perpendicular to said longitudinal axis A, said main extension B of said at least two slots (3) being in said plane P, and that a predetermined number of planes P with slots (3) are provided along said tube (1), wherein the lengths L of said slots (3) in the same perpendicular plane P are essentially the same, and that said lengths L of said slots (3) in different planes vary along said longitudinal extension of said tube (1) according to a predefined pattern.

(II) The tube according to embodiment (I), wherein said slots (3) in said same perpendicular plane P are separated by a slot separation part (4).

(III) The tube according to any of embodiments (I)-(II), wherein said slots (3) in said same perpendicular plane P are equally distributed around said circumference of said tube (1).

(IV) The tube according to any of embodiments (I)-(III), wherein according to said predefined pattern said lengths L of said slots (3) decreases in a proximal direction of said tube (1).

(V) The tube according to embodiment (VI), wherein said lengths L of said slots (3) decreases continuously.

(VI) The tube according to any of the preceding embodiments, wherein according to said predefined pattern said lengths L of said slots (3) are equal in a distal section (5) of said tube (1).

(VII) The tube according to embodiment (VI), wherein the length $L_4$, along said longitudinal axis A, of said distal section (5) is approximately 150 mm.

(VIII) The tube according to any of the preceding embodiments, wherein said length L of a slot (3) is defined by a slot angle $\alpha$, being the center angle of said perpendicular plane P.

(IX) The tube according to embodiment (VIII), wherein said slot angle is $0°<\alpha<160°$.

(X) The tube according to embodiment (IX), wherein said slot angle $\alpha$ is approximately 40° in said distal section (5) of said tube (1).

(XI) The tube according to any of embodiments (VIII)-(X), wherein said slot angle $\alpha$ decreases from approximately 40° to approximately 0° in a proximal section (6) of said tube (1).

(XII) The tube according to embodiment (XI), wherein the length $L_4$, along said longitudinal axis A, of said proximal section (6) is approximately 200 mm.

(XIII) The tube according to any of embodiments (VI)-(VII) or (IX)-(XII), wherein said distal section (5) and said proximal section (6) are arranged adjacent to each other.

(XIV) The tube according to any of the preceding embodiments, wherein the slots (3) in said perpendicular plane P are displaced in relation to the slots (3) in an adjacent perpendicular plane P.

(XV) The tube according to any of the preceding embodiments, wherein said tube (1) is adapted to extend at least partly along the length of a guide wire, a sensor guide wire, or a catheter.

(XVI) The tube according to any of the preceding embodiments, wherein said tube (1) is provided with a coating covering all, or parts of, said slots (3).

(XVII) The tube according to any of the preceding embodiments, wherein adjacent perpendicular planes P are separated by a predetermined separation distance d, being approximately 0.1 mm.

(XVIII) The tube according to any of the preceding embodiments, wherein said predetermined number of planes P is approximately in the interval 1000-5000.

(XIX) The tube according to any of the preceding embodiments, wherein said width W of a slot (3) being approximately 0.05 mm.

(XX) The tube according to any of the preceding embodiments, wherein said tube (3) having an inner diameter of approximately 0.25 mm, and an outer diameter of approximately 0.35 mm.

(XXI) A sensor guide wire for intravascular measurements of at least one physiological or other variable in a living body, the sensor guide wire (8) having a proximal region (9), a distal sensor region (10) and a tip region (11), the sensor guide wire (8) comprising:
a sensor element (12) arranged in said sensor region (10), and comprising a sensor portion (13), for measuring said variable and to generate a sensor signal in response to said variable,
wherein said sensor guide wire (8) comprises a tube (1) according to any of embodiments (I)-(XX), and in that said tube (1) extends at least partly along said proximal region (9) of said sensor guide wire (8).

(XXII) A sensor guide wire according to embodiment (XXI), wherein said tube (1) extends at least partly along said distal sensor region (10).

(XXIII) A sensor guide wire according to embodiment (XXII), wherein said tube (1) is adapted to enclose at least a part of said sensor element (12), and is provided with at least a first sensor opening (7) in said distal sensor region (10).

(XXIV) A sensor guide wire according to any of embodiments (XXII)-(XXIII), wherein said sensor region (10) is an integrated part of said tube (1).

(XXV) A sensor guide wire according to any of embodiments (XXI)-(XXII), wherein said sensor guide wire is provided with a jacket (15) adapted to enclose at least a part of said sensor element (12), and being provided with at least a first sensor opening (7) in said distal sensor region (10).

(XXVI) A sensor guide wire according to any of embodiments (XXI)-(XXV), wherein said jacket (15) is attached to said tube (1).

(XXVII) A sensor guide wire according to any of embodiments (XXI)-(XXVI), wherein no core wire is arranged to extend along said proximal region (9).

(XXVIII) A sensor guide wire according to any of embodiments (XXI)-(XXVII), wherein no core wire is arranged to extend along said distal sensor region (10).

(XXIX) A sensor guide wire according to any of embodiments (XXI)-(XXVIII), wherein said proximal section (6) of said tube (1) is arranged in said proximal region (9) of said sensor guide wire (8).

(XXX) A sensor guide wire according to any of embodiments (XXI)-(XXIX), wherein said distal section (5) of said tube (1) is arranged in said proximal region (9) of said sensor guide wire (8).

(XXXI) A sensor guide wire according to any of the preceding embodiments, wherein a security string extends from a proximal end to a distal end (14) of said sensor guide wire (8).

(XXXII) A sensor guide wire according to embodiment (XXXI), wherein said security string is a flexible wire running inside said tube (1).

The present invention is not limited to the above-described preferred embodiments. Various alternatives, modifications and equivalents may be used. Therefore, the above embodiments should not be taken as limiting the scope of the invention.

What is claimed is:

1. A sensor guide wire for an intravascular measurement of at least one variable in a living body, the sensor guide wire comprising:
    a sensor element comprising a sensor portion configured to measure the variable and to generate a sensor signal in response to the variable; and
    a tube that extends at least partly along the sensor guide wire,
    wherein the tube comprises a tube wall having a plurality of through-going slots,
    wherein each slot of the plurality of through-going slots has an elongated shape and extends circumferentially around the tube,
    wherein each slot is assigned to a perpendicular plane that runs perpendicular to a longitudinal axis of the tube such that the slots extend in their respective planes,
    wherein the planes to which the sets of slots are assigned are provided along the tube,
    wherein adjacent perpendicular planes are separated by a predetermined separation distance,
    wherein the slots are divided into a first set of slots, all of which are located proximal of the sensor element, and a second set of slots, all of which are located distal of the sensor element, and
    wherein a separation distance between adjacent perpendicular planes of the first set of slots located proximal of the sensor element is greater than a separation distance between adjacent perpendicular planes of the second set of slots located distal of the sensor element, such that a portion of the tube located proximal of the sensor element is less flexible than a portion of the tube located distal of the sensor element, and
    wherein a slot angle of the slots in the second set of slots is greater than a slot angle of the slots in the first set of slots, the slot angle of a slot being defined as an angle between lines extending perpendicularly from a center axis of the tube to two ends of that slot.

2. The sensor guide wire according to claim 1, wherein the tube encloses at least a part of the sensor element, and wherein the tube includes at least a first sensor opening.

3. The sensor guide wire according to claim 1, wherein the sensor guide wire includes a jacket that encloses at least a part of the sensor element, and wherein the jacket includes at least a first sensor opening.

4. The sensor guide wire according to claim 3, wherein the jacket is attached to the tube.

5. The sensor guide wire according to claim 1, wherein no core wire is arranged to extend along a proximal region of the sensor guide wire.

6. The sensor guide wire according to claim 1, wherein no core wire is arranged to extend along a distal sensor region of the sensor guide wire.

7. The sensor guide wire according to claim 1, wherein a security string extends from a proximal end of the sensor guide wire to a distal end of the sensor guide wire, and wherein the security string is a flexible wire running inside the tube.

8. The sensor guide wire according to claim 1, wherein a separation distance between all of the adjacent perpendicular planes of the first set of slots located proximal of the sensor element is the same, and a separation distance between all of the adjacent perpendicular planes of the second set of slots located distal of the sensor element is the same.

9. The sensor guide wire according to claim 1, wherein the slot angle of the slots in the first set of slots is about 95°, and the slot angle of the slots in the second set of slots is about 105°.

* * * * *